United States Patent [19]

Huffman

[11] Patent Number: 4,533,323
[45] Date of Patent: Aug. 6, 1985

[54] MOUNTING FOR DENTAL MODEL ARTICULATORS

[75] Inventor: Ronald E. Huffman, Tucson, Ariz.

[73] Assignee: KV33 Corporation, Tucson, Ariz.

[21] Appl. No.: 533,416

[22] Filed: Sep. 19, 1983

Related U.S. Application Data

[63] Continuation-in-part of Ser. No. 486,897, Apr. 20, 1983, Pat. No. 4,449,930.

[51] Int. Cl.³ .............................................. A61C 11/00
[52] U.S. Cl. ........................................ 433/60; 433/64
[58] Field of Search ..................................... 433/60, 64

[56] References Cited

U.S. PATENT DOCUMENTS 750,203  1/1904  Knight ................................... 433/64
2,138,254 11/1938 Mink ...................................... 433/63

FOREIGN PATENT DOCUMENTS 2922187 12/1980 Fed. Rep. of Germany ........ 433/60

Primary Examiner—Robert Peshock
Attorney, Agent, or Firm—Cahill, Sutton & Thomas

[57] ABSTRACT

A mounting cooperatively associated with the rear face of each cast of a pair of dental model casts interconnects one of opposed parts of an articulator to secure the articulator to the dental model. Each mounting includes at least one cast insertable locking member supporting one element of a ball and socket joint which joint is disposed intermediate the respective cast and the articulator.

17 Claims, 3 Drawing Figures

U.S. Patent  Aug. 6, 1985  4,533,323
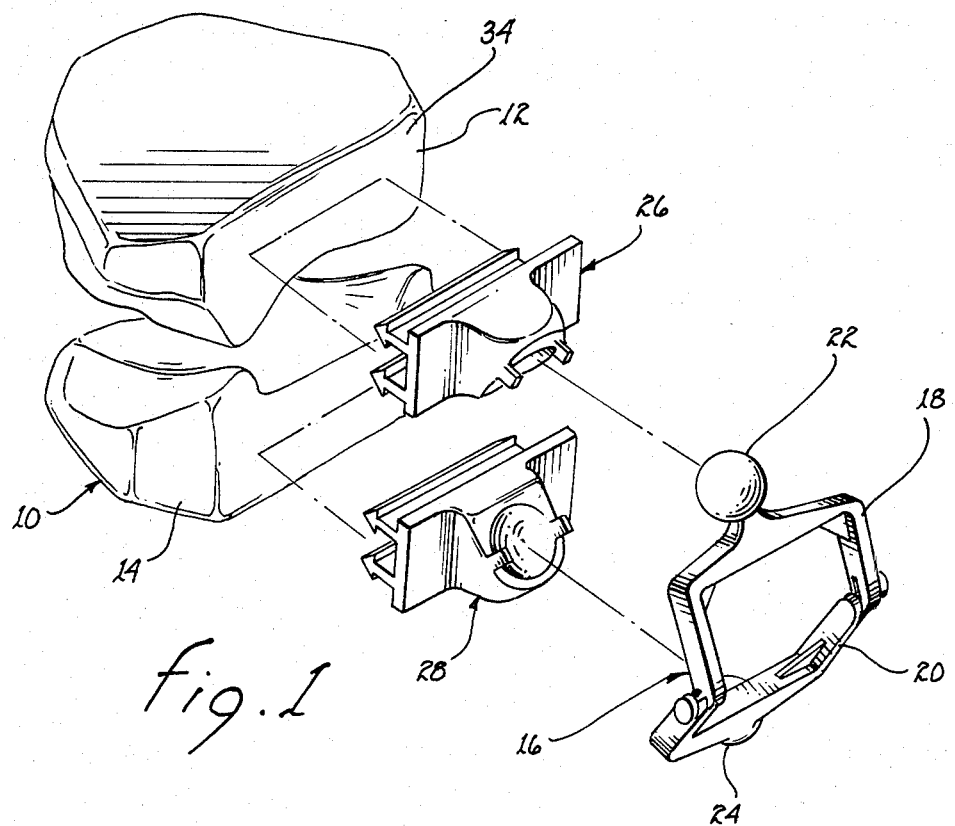
fig. 1
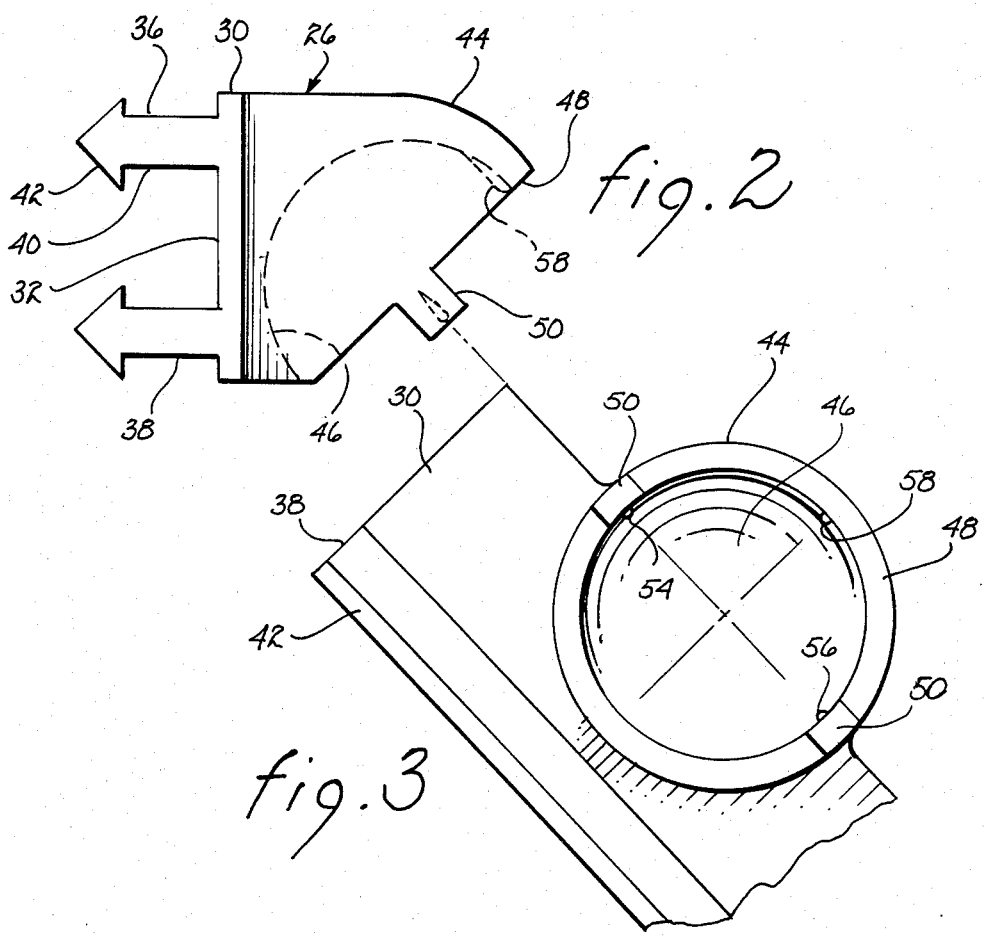
fig. 2
fig. 3

MOUNTING FOR DENTAL MODEL ARTICULATORS

The present application describes an invention related to U.S. Letters Pat. No. 4,382,787 issued May 10, 1983 entitled "DENTAL MODEL ARTICULATOR" and is a continuation-in-part application of a copending application entitled "DENTAL MODEL ARTICULATOR", Ser. No. 486,897, filed Apr. 20, 1983, now U.S. Pat. No. 4,449,930, issued 5/22/84 both of which are assigned to the present assignee and describe inventions made by the present inventor.

Correlators or articulators for use with casts of a dental model to develop prosthetic dentures or denture elements have been used for a number of years. These articulators range from a very simple device affording only fixed pivotal movement between a pair of casts to highly sophisticated and mechanically complex devices which are capable of simulating the full range of occlusal and masticatory registration unique to any patient. The relatively simple devices are generally inadequate to provide sufficiently accurately registered prosthetic restoration to avoid extensive visits with a dentist to obtain adjustments thereof while the very complex devices are time consuming to operate and require extensive training to use properly. In either situation, the costs incurred to the patient are substantial. Moreover, none of the prior art articulators permit disengagement of the cats from registration with one another without extensive realignment upon reengagement. Thus, a technician is usually forced to perform his work while the casts are mounted on the articulator. Such an environment is difficult to work in with speed and accuracy.

Each of the following listed United States patents are directed to dental articulators and structures for attaching them to the dental model. The articulators incorporate lockable ball and socket elements to afford pivotal movement and extensible members to afford translational movement: Nos. 175,046, 530,524, 537,812, 565,326, 981,430, 1,736,006, 1,841,728, 2,571,280, 2,600,899, 2,608,762, 2,621,407, 2,765,533, 4,169,314, 4,196,518 and Belgian Pat. No. 572,850.

An articulator and method of attaching it to a dental model and which articulator provides structure to effect a simple hinged movement without provision of mechanical structure for defining translatory movement of multi-axis pivotal movement is disclosed in U.S. Pat. No. 2,430,177. Other United States Patents describing articulators and methods for attaching them to a dental model include Nos. 824,096, 3,429,045 and 3,466,750.

The present invention is directed to a mounting for attaching each of opposed parts of an inexpensive throwaway articulator to a cast of a dental model. The mounting includes one element of a ball and socket joint; the other element is included with the attached part of the articulator. At least one locking member is formed in the mounting for penetrable and mechanically lockage insertion into the rear face of the respective casts. Such insertion may be effected while the cast is still in a fluid state during formation thereof and before setting of the cast material. Alternatively, the locking member may be inserted subsequent to setting of the cast after an appropriately sized cavity has been formed therein to receive the locking member; adhesive or packing of cast material may be used to effect a mechanical locking action. The mounting may be inserted laterally or vertically anywhere along the rear face, which freedom of positioning permits rapid attachment and precise positioning of the mounting to accommodate, in conjunction with the parameters of the articulator, variations in size and depth of the casts.

A primary object of the present invention is to provide mountings for attaching an articulator to the casts of a dental model.

Another object of the present invention is to provide a mounting lockingly attachable to a cast of a dental model during formation of the cast.

Still another object of the present invention is to provide a mounting useable post curing of a dental model cast for attaching an articulator thereto.

Yet another object of the present invention is to provide a mounting for supporting a ball and socket joint intermediate a dental model cast and an articulator.

A further object of the present invention is to provide a penetrably mechanically lockable articulator mounting.

A still further object of the present invention is to provide a method for attaching articulators to dental model casts.

A yet further object of the present invention is to provide a method for accommodating size variations of dental model casts to be interconnected with an articulator.

These and other objects of the present invention will become apparent to those skilled in the art as the description thereof proceeds.

The present invention will be described with greater specificity and clarity with reference to the following drawings, in which:

FIG. 1 is an isometric view of the mounting and related elements;

FIG. 2 is a side view of the mounting; and

FIG. 3 is a front view of the mounting.

Referring to FIG. 1, there is shown a complete dental model 10 having a pair of mating dental model casts 12, 14, simulative of the original dentures and the condition requiring restoration or correction. An articulator 16 is attachable to the casts to maintain them positionally simulative of the natural relationships portrayed when substantially in parallel relationship at one limit of the range of relative movement. The articulator includes a pair of interconnecting parts of brackets 18, 20, pivotally attached to one another. These brackets are of resilient flexible material sufficient to accommodate relative movement about all axis and within all planes between the casts in simulation of the operative range and pattern of the original dentures.

Brackets 18, 20 include balls 22, 24, respectively, of a ball and socket joint to be developed for attaching articulator 16 to the casts of dental model 10. The socket of each ball and socket joint is formed by mountings 26, 28. As depicted by the dashed lines, mounting 26 is cooperatively associated with cast 12 and mounting 28 is cooperatively associated with cast 14. Upon attachment of the balls of articulator 16 with the respective mountings, the casts of dental model 10 may be articulated.

Referring to FIGS. 2 and 3, the structure of mountings 26, 28 will be described. Mounting 26 may include a central plate member 30 which plate member serves several purposes. First, it provides a flat surface 32 for bearing against a correspondingly flat surface of rear face 34 of cast 12. Juxtapositioning of these two surfaces provides structural stability therebetween to prevent unwanted tilting or angular deviation. Moreover, a substantial coincident surface area is provided for bonding if the latter is to be performed and bring about an increase in the structural rigidity therebetween.

Second, plate member 30 supports one or more locking means 36, 38, 42 extending rearwardly therefrom. The locking means may be formed as a flange 40 having an expanded rear edge portion 42. In example, the rear edge portion may be configured like an arrowhead in cross-section, as shown in FIG. 2. When the locking means is enveloped by the settable or hardenable material of which cast 12 is made, the expanded rear edge portion will provide a physical constraint against withdrawal of mounting 26 since such withdrawal cannot be accomplished without breakage of the cast.

Third, a structure 44 extends forwardly from plate member 30 and defines a socket 46 having a perimeter 48. A pair of flexible tabs 50, 52 extend from perimeter 48 to grippingly receive and retain a ball (such as ball 22) inserted within the socket and constrain withdrawal of the ball. Such retention permits positional adjustment of casts 12 and 14 with articulator 16 attached thereto to locate the casts in parallel relationship at one limit of the range of relative movement prior to fixation of the interconnection between the articulator and the casts.

To accommodate for conventional manufacturing tolerances and assure positive frictional engagement between the tabs and the ball, one of tapered ridges 54, 56 may be formed on the inside surface of each of the tabs 50, 52, respectively. To further accommodate for conventional manufacturing tolerances which may prevent other than a perfect spherical match between socket 46 and ball 22, a radially extending tapered protrusion 58 may be formed upon the surface of the socket. This ridge bears against the ball upon insertion to maintain the ball in frictional contact with as much of the socket surface area as is possible and depending upon size variations therebetween caused by manufacturing tolerances. Protrusion 58 also provides frictional engagement intermediate the ball and the socket to prevent inadvertent or unwanted rotational movement therebetween during positioning of casts 12, 14 and articulator 16 prior to fixing of the angular relationship between each socket and its respective ball.

Once casts 12, 14 have been positioned with respect to one another at one limit of the range of relative movement therebetween, the angular and positional relationship of articulator 16 with respect to mountings 26 and 28 is fixed. Such fixing may be effected by bonding each ball within its respective socket. Any of many commercially available adhesives compatible with the materials employed for the articulator and the mountings may be used as the bonding agent.

Preferably, mountings 26, 28 are attached to the rear faces of the respective casts prior to complete setting of the material of the casts and while the material is sufficiently fluid or plastic to permit penetration of the locking means and subsequent flow of material about the expanded rear edge portions and adjacent to the supporting flanges. The stage in the creation of the casts at which point a mounting is melded therewith is a matter of proficiency and expertise of the technician.

Alternatively, cavities may be formed in the rear surface of a cast to receive the locking means and thereafter filled with further casting material to achieve the above discussed mechanical lock. Other techniques may become apparent through use and familiarity with the mountings.

Depending upon manufacturing considerations and other criteria, the mounting may be adapted to support the ball of the ball and socket joint and the articulator may be adapted to support the socket of the ball and socket joint.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A one piece mounting for securing one part of an articulator to the rear face of a dental model cast made of flowable, curable, hardenable material, said mounting comprising in combination:

(a) plate means for bearing against the rear face and for positionally locating said mounting with respect to the dental model cast;
    (b) a structure extending from said plate means for defining an element of a ball and socket joint; and
    (c) locking means extending from another side of said plate means for insertion into th dental model cast through the rear face, said locking means including laterally expanded means for mechanically locking said member with the dental model cast upon curing of flowable, curable and hardenable material enveloping said laterally expanded means within the dental model cast;

whereby, said mounting, upon mating of the other element of the ball and socket joint disposed upon the articulator with said structure, secures the dental model cast to the articulator.

2. The mounting as set forth in claim 1 wherein said mechanical locking means includes a flange for insertion into the dental model cast.

3. The mounting as set forth in claim 2 wherein said laterally expanded means comprises an arrowhead shape in cross-section.

4. The mounting as set forth in claim 2 including a further flange for insertion into the dental model cast.

5. The mounting as set forth in claim 4 wherein each said laterally expanded means comprises an arrowhead shape in cross-section.

6. The mounting as set forth in claim 1 wherein said structure comprises a socket of the ball and socket joint.

7. The mounting as set forth in claim 6 wherein said socket includes a perimeter and retaining means extending from said perimeter for constraining withdrawal of the ball of the ball and socket joint after insertion of the ball within said socket.

8. The mounting as set forth in claim 7 wherein said retaining means comprises a pair of tabs extending from said perimeter at diametrically opposed locations.

9. The mounting as set forth in claim 8 wherein at least one of said tabs includes a radially inwardly oriented ridge for frictionally engaging a ball inserted within said socket.

10. The mounting as set forth in claim 8 wherein said socket includes a protrusion for biasing a ball inserted within said socket against the opposing socket surface.

11. The mounting as set forth in claim 6 wherein said socket includes a protrusion for biasing a ball inserted within said socket against the opposing socket surface.

12. The mounting as set forth in claim 8 wherein said mechanical locking means includes a flange for insertion into the dental model cast.

13. The mounting as set forth in claim 12 including a further flange for insertion into the dental model cast.

14. The mounting as set forth in claim 13 wherein said said laterally expanded means comprises an arrowhead shape in cross-section.

15. The mounting as set forth in claim 1 wherein said plate means includes a planar surface for juxtapositioning with the rear surface of the dental model cast and from which said locking means extends.

16. A method for attaching a monolithic mounting to the rear surface of each cast of a dental model to interconnect the casts with one another through the arms of an articulator, each mounting including plate means, locking means extending from one side of the plate means and one part of a ball and socket joint extending from another side of the plate means, said method comprising the steps of:
(a) forming each cast from a hardenable material;
(b) attaching one of the mountings to each cast by inserting the locking means of the mounting through the rear face of the respective cast and into hardenable material within the respective cast, said step of attaching including the step of limiting penetration of the locking means into the casts by interference of the plate means of the mountings with the rear face of the respective cast;
(c) at least partially enveloping the locking means of each mounting with hardenable material to develop a mechanical lock therebetween upon hardening of the material;
(d) mating the one part of a ball and socket joint extending from each mounting with another part of the ball and socket joint extending from one of the arms of the articulator to form a ball and socket joint therebetween;
(e) temporarily retaining engaged the parts of each ball and socket joint;
(f) aligning the casts of the dental model with one another; and
(g) permanently fixing each ball and socket joint to preclude movement and separation between the mounting and the engaged arm of the articulator.

17. The method as set forth in claim 16 wherein said step of retaining includes the step of biasing the ball against a part of the surface of the socket.

* * * * *